(12) United States Patent
Bayerl

(10) Patent No.: US 8,609,147 B2
(45) Date of Patent: Dec. 17, 2013

(54) USE OF DEUTERIUM OXIDE FOR TREATMENT OF HERPES VIRUS-BASED DISEASES OF THE SKIN

(75) Inventor: Thomas M. Bayerl, London (GB)

(73) Assignee: D2 Bioscience Group Ltd., Hamilton (BM)

( * ) Notice: Subject to any disclaimer, the term of this patent is extended or adjusted under 35 U.S.C. 154(b) by 916 days.

(21) Appl. No.: 12/168,583

(22) Filed: Jul. 7, 2008

(65) Prior Publication Data

US 2009/0011022 A1 Jan. 8, 2009

(30) Foreign Application Priority Data

Jul. 5, 2007 (DE) .................. 10 2007 031 397

(51) Int. Cl.
*A01N 59/00* (2006.01)
*A61K 33/00* (2006.01)

(52) U.S. Cl.
USPC ........................................ 424/600

(58) Field of Classification Search
None
See application file for complete search history.

(56) References Cited

U.S. PATENT DOCUMENTS

| | | | | |
|---|---|---|---|---|
| 5,028,431 | A * | 7/1991 | Franz et al. ................... | 424/449 |
| 5,223,269 | A | 6/1993 | Liepins et al. | |
| 5,233,269 | A | 8/1993 | Lien | |
| 5,788,953 | A * | 8/1998 | Somlyai .......................... | 424/59 |
| 6,009,876 | A * | 1/2000 | Yavitz ........................... | 128/898 |
| 6,977,164 | B2 * | 12/2005 | WalkerPeach et al. .... | 435/91.33 |
| 7,132,452 | B2 * | 11/2006 | Lee et al. ...................... | 514/570 |
| 7,767,215 | B2 * | 8/2010 | McClellan et al. ........... | 424/401 |
| 2002/0183380 | A1 | 12/2002 | Hunter et al. | |
| 2004/0086453 | A1 | 5/2004 | Howes | |
| 2004/0234450 | A1 | 11/2004 | Howes et al. | |
| 2005/0187212 | A1 * | 8/2005 | Ohki et al. ................. | 514/226.5 |
| 2007/0129282 | A1 * | 6/2007 | Ahlem et al. ..................... | 514/2 |
| 2007/0141074 | A1 | 6/2007 | Schubert | |
| 2008/0113035 | A1 | 5/2008 | Hunter et al. | |
| 2009/0131486 | A1 | 5/2009 | Hansen et al. | |
| 2010/0196285 | A1 | 8/2010 | Bayerl et al. | |
| 2010/0329994 | A1 | 12/2010 | Bayerl et al. | |
| 2011/0076331 | A1 | 3/2011 | Bayerl et al. | |

FOREIGN PATENT DOCUMENTS

| | | |
|---|---|---|
| DE | 3019434 | 1/1982 |
| DE | 4427690 | 2/1996 |
| DE | 102006026464 | 12/2007 |
| EP | 0 751 778 | 1/1997 |
| EP | 0 893 123 | 1/1999 |
| EP | 0893123 | 1/1999 |
| EP | 1 070 502 | 1/2001 |
| EP | 2110132 | 10/2009 |
| WO | 96/03996 | 2/1996 |
| WO | 99/62510 | 9/1999 |
| WO | 2005/016234 | 2/2005 |
| WO | 2005/063281 | 7/2005 |
| WO | 2006/022460 | 3/2006 |
| WO | 2007/129962 | 11/2007 |
| WO | 2008/046407 | 4/2008 |

OTHER PUBLICATIONS

Lindwall, et al. (Feb. 9, 2006) Journal of Investigative Dermatology, 126(4): 841-48.*
Wainwright (2003) International Journal of Antimicrobial Agents, 21(6): 510-20.*
Muller-Breitkreutz, et al. (2995) Journal of Photochemistry and Photobiology, 30: 63-70.*
http://en.wikipedia.org/wiki/Norwegian_heavy_water_sabotage. No date of publication. "Norwegian Heavy Water Sabotage", Publisher: Wikipedia; No Edition or volume; Whole Web page is pertinent. No Author Provided.*
Nancy Oleinick, http://www.photobiology.info/Oleinick.html, 2005, Publisher: Photobiologial Sciences Online, no location given; No edition; No volume; Whole Web Page is Pertinent.*
http://en.wikipedia.org/wiki/Heavy_water; No author; No date of Publication; "Heavy Water", Publisher: Wikipedia, no location given; No edition; No volume; Whole Web Page is Pertinent.*
http://www.sircuitskin.com/inc/sdetail/11707; Author is Sircuit Cosmeceuticals®; No Title; Publisher: Sircuit Cosmeceuticals®; No location given; No edition, No volume; Whole Web Page is Pertinent.*
Email Containing Google Search Results, From James H. Jenkins (ASRC), USPTO, dated Aug. 25, 2011; no publisher, no edition, no volume, whole attached web page is pertinent (pp. 1-2, p. 1 pertinent).*
Ravariu, et al. (2004) "A silicon Nanoporous Membrane Used for Drug Delivery", Semiconductor Conference, CAS 2004 Proceedings, 2004 International, pp. 101-104 (IEEE) NO edition; no volume, p. 101 pertinent.*
Neyts, et al. (1999) Antimicrobial Agents and Chemotherapy, 43(12): 2885-92.*
Cryan, "Carrier-based strategies for targeting protein and peptide drugs to the lungs," *AAPS Journal*, vol. 7, No. 1, pp. E20-E41.
Čuma et al., "Influence of Isotopic Substitution on Strength of Hydrogen Bonds of Common Organic Groups," *Journal of Physical Organic Chemistry*, 1997, vol. 10, pp. 383-395.
König et al., "Molecular dynamics of water in oriented DPPC multilayers studied by quasielastic neutron scattering and deuterium-nuclear magnetic resonance relaxation," *J. Chem. Phys.*, 1994, vol. 100, pp. 3307-3316.
Koshkina et al., "Paclitacel liposome aerosol treatment induces inhibition of pulmonary metastases in murine carcinoma model," *Clinical Cancer Research*, 2001, vol. 7, pp. 3258-3262.
Kushner et al., "Pharmacological uses and perspectives of heavy water and deuterated compounds," *Can J Physiol Pharmacol*, Feb. 1999, vol. 77, No. 2, pp. 79-88.
Laissue et al., "Survival of tumor-bearing mice exposed to heavy water or heavy water plus methotrexate," *Cancer Research*, 1982, vol. 42, No. 3, pp. 1125-1129.

(Continued)

*Primary Examiner* — Robert M Kelly
(74) *Attorney, Agent, or Firm* — McDonnell Boehnen Hulbert & Berghoff LLP

(57) ABSTRACT

The present invention relates to the use of deuterium oxide ($D_2O$) for prevention and/or treatment of virus-based diseases of the skin, in particular herpes virus-based and verrucal virus-based diseases of the skin.

20 Claims, 3 Drawing Sheets

(56) References Cited

OTHER PUBLICATIONS

McKeough et al., "Comparison of New Topical Treatments for Herpes Labialis," *Arch Dermatol*, 2001, vol. 137, pp. 1153-1158.

Mello et al., "Revealing the world of RNA interference," *Nature*, Sep. 2004, vol. 431, pp. 338-342.

Reinl et al., "Time-resolved Infrared ATR Measurements of Liposome Transport Kinetics in Human Keratinocyte Cultures and Skin Reveals a Dependence on Liposome Size and Phase State," *J. Invest. Dermatol*, 1995, vol. 105, No. 2, pp. 291-295.

Takeda et al., "Mechanisms of cytotoxic effects of heavy water (deuterium oxide: D20) on cancer cells," *Anticancer Drugs*, Sep. 1998, vol. 9, No. 8, pp. 715-725, Abstract only.

Takeda et al., "Mechanisms of cytotoxic effects of heavy water (deuterium oxide: D20) on cancer cells," *Anticancer Drugs*, Sep. 1998, vol. 9, No. 8, pp. 715-725.

Chapter 171: Gram-positive cocci (Pneumococcal infections) In: Beers et al.: The Merck Manual, 18th Edition 2006, Merck research laboratories, USA, XP002574619, Seiten 1-2991.

Lifson (02 180 (deuterium oxide) method for C02 output in small mammals and economic feasibility in man, Journal of Applied Physiology, Oct. 1975, vol. 39, No. 4) abstract only.

White et al., Effect of Colchicine, vinblastine, D20 and cytochalasin B on elastase secretion, protein synthesis and fine structure of mouse alveolar macrophages, Journal of the Reticuloendothelial Society Apr. 1981, Bd. 29, Nr. 4, Apr. 1981, S. 295-304.

Pauwels, Global Strategy for the diagnosis, Management, and Prevention of Chronic Obstructive Pulmonary Disease, American Journal of Respiratory and Critical care Medicine, 2001, vol. 163 pp. 1256-1276.

Stein ("Catalysis by Human Leukocyte Elastase: Substrate Structural Dependence of Rate-Limiting Protolytic Catalysis and Operation of the Charge Relay System," J . Am. Chem. SOC1. 983, 105,51 11-51 16).

Giudice et ai, "Cloning and Primary Structural Analysis of the Bullous Pemphigoid Autoantigen BP180," Journal of Investigative Dermatology (1992) 99, 243-250).

Liu et al., "A critical role for neutrophil elastase in experimental bullous pemphigoid," J Clin Invest. 2000; 105 (1 ):113-123.

Bastow T J et al: "H and C NMR studies of water and heavy water absorption in poly(vinyl alcohol) hydrogels", Journal of Membrane Science, Elsevier Scientific Publ. Company. Amsterdam, NL, Bd. 131, Nr. 1-2, Aug. 6, 1997, Seiten 207-215.

Carp, R.I. and Kritchevsky, D.: Influence of heavy water (D2O) on the multiplication of adeno and mengo virus. In: Experientia, 1967, vol. 23, S. 786-787.

\* cited by examiner

USE OF DEUTERIUM OXIDE FOR TREATMENT OF HERPES VIRUS-BASED DISEASES OF THE SKIN

CROSS-REFERENCE TO A RELATED APPLICATION

This application claims priority to German Application No. 102007031397.9-41, filed Jul. 5, 2007, in its entirety.

FIELD OF THE INVENTION

The present invention relates to the use of deuterium oxide ($D_2O$) for prevention and/or treatment of virus-based diseases of the skin, in particular herpes virus-based diseases of the skin.

BACKGROUND OF THE INVENTION

Diseases caused by viruses (viral infections) are widespread throughout the world and constitute a serious problem in medicine, in particular because of the high variability, adaptability and mutation rate of viruses. Viruses are small particles of approximately 15 to 400 nm, which are unable to replicate themselves but instead require a host cell to do so. Depending on their host specificity, viruses are differentiated according to those which attack animals (invertebrates and vertebrates), plants, bacteria or algae, fungi and protozoa. Viral infections are characterized in general by a high replication rate of the viral particles in the infected host cells, which can be described with an exponential law. The general reproduction cycle of viruses takes place via injection of their nucleic acid (RNA or DNA) into the host cell, in which the replication of the nucleic acid takes place by utilizing the replication apparatus of the host cell. Replication of viruses may take place either in the lytic or lysogenic cycle. In the lytic cycle (active infection), the viral nucleic acid is replicated in the cell nucleus of the host cell after injection of the nucleic acid, the new viral particles are assembled in the cytoplasm, whereupon the host cell is ultimately lysed (destroyed) and the viruses are released. Viruses released in this way then infect other host cells. In the lysogenic cycle, the nucleic acid (DNA) of the virus is integrated into the genome of the host cell, where it remains without destroying the host cell. This lysogenic cycle may be converted to a lytic cycle as described above due to external influences (e.g., UV radiation, addition of mutagenic substances).

Virus-based diseases of the skin are understood in general to be diseases of the skin caused by a virus. Virus-based diseases of the skin include in particular diseases and/or infections which are caused by herpesviruses and are also referred to colloquially simply as herpes. Herpesviruses occur widely in vertebrates, in particular in mammals and especially in humans, horses, swine, cattle, goats, sheep, cats and dogs.

Human pathogenic herpesviruses (HHV) are differentiated according to alpha, beta, and gamma-herpesviruses (HHV-1 through HHV-8), where the alpha and gamma viruses are also among viruses that can infect animals, e.g., the horse (equine herpesvirus), cattle (bovine herpesvirus), swine (porcine herpesvirus), cat (feline herpesvirus), dog (canine herpesvirus) and chicken (chicken herpesvirus 1).

Of the human pathogenic herpesviruses, those which infect humans, in particular the alpha-herpesviruses, are of great importance. The alpha-herpesviruses include herpes simplex virus 1 (HSV-1), herpes simplex virus 2 (HSV-2) and varicella zoster virus (VZV).

The diseases of the skin caused by herpes simplex viruses HSV-1 and HSV-2 include, for example, herpes labiales, also known as fever blisters or herpes of the lips, and herpes nasalis, both caused primarily by HSV-1, keratoconjunctivitis herpetica, stomatitis herpetica, herpes facialis, herpes buccalis, herpes genitales, herpes perianalis, herpes glutealis. Varicella zoster viruses (VZV) cause chickenpox and shingles, for example.

Virologists have estimated that 80% of the population worldwide has latent HSV-1 infections and 30% HSV-2. HSV-1 and HSV-2 are closely related to one another and have a high percentage of identical nucleotide sequences. Although HSV-1 infects primarily the oral and facial area, HSV-2 occurs mainly in the genital area.

Alpha-herpesviruses usually first infect epithelial cells such as skin cells, mucous cells and mucosal cells, followed by a marked replication of the virus in the host cell and death of the infected host cell.

For example, HSV-1 will spread in skin cells and/or mucosal cells of the face and mouth, usually causing local damage, namely in the form of a vesicle. Antibodies neutralize the viruses in the vesicles after a short period of time, but viruses are also released by lysis of the infected host cells before a humoral immune response can take place. The viruses thereby released also infect certain nerve cells (neurons) by adhering to receptors on the nerve endings in the mouth, which can lead to the neural node of the facial nerve (trigeminus). The viral DNA penetrates into an axon, enters the cytoplasm of the nerve cells and finally enters the cell nucleus where the viral DNA is incorporated into the genome of the nerve cell, leading to a latency in which only a few viral genes are expressed (lysogenic cycle). Various external stimuli can be lead to renewed activation of the virus, i.e., the transition from latency and/or the lysogenic cycle to the lytic cycle which ultimately results in destruction (lysis) of the nerve cell. Such stimuli include, for example, immunosuppression, stress, hormone fluctuations, physical or emotional stresses, fever (which is also why they are called fever blisters), UV radiation, tissue damage and in many cases an immunological weakness. The incidence of such activation of HSV-1 probably depends on both genetic and environmental factors, and both age and hormone changes can play a role. The viral progeny occurring as part of an activation are first transported by the axon to the site and/or the region of the original skin infection where they again create vesicles or blisters (fever blisters) by infection of and replication in the skin cells and/or mucosal cells. Even if these viruses are again neutralized by the immune system, it is impossible to free the body completely of HSV-1 through the immune system because additional nerve cells in which the viral DNA remains integrated into the genome (latency) are constantly being infected.

Additional virus-based diseases of the skin, which are widespread, include diseases and/or infections which are caused by verrucal viruses and are referred to colloquially as warts.

Warts (verrucae) are small, flat or slightly raised, sharply delineated and highly contagious (under some circumstances) but usually benign epithelial tumors and/or proliferations of skin, in particular epidermis. They occur on the hands and feet in particular. Warts usually have a thick, horny, partially fissured coating of squamous epithelial cells beneath which there are soft tissue of keratinocytes.

These diseases of the skin (warts) are caused by a virus infection, mainly by papillomaviruses, in particular human papillomaviruses (HPV) such as verrucae vulgares, verrucae planae juvenilis, verrucae plantares, condylomata acuminata, verrucae planae, verrucae filiformes and molluscipox viruses, e.g., molluscum contagiosum. The infection occurs through small injuries in the skin and/or mucosa. Verruca viruses infect skin cells of vertebrates, in particular mammals and especially humans.

Warts are fundamentally benign proliferations which may cause severe pain in certain areas, e.g., in the genital area and may in extremely rare cases develop into a malignancy. They may also become a cosmetic problem due to their appearance and frequent further propagation on the skin. Treatment of warts is very tedious. So far various therapeutic approaches have been developed:

Surgical removal
Electrocoagulation
Laser removal
Cryosurgery (freezing)
Cauterization (use of electric current or caustic agents)
Cytostatics such as 5-fluorouracil, podophyllotoxin and podophylline which are painted on the warts.

All the therapeutic approaches listed above are, however, based on treatment of the sequelae of a verrucal virus infection, not on inhibition or prevention of viral replication.

In contrast with that, the herpesvirus-based diseases of the skin mentioned above are generally treated by using antiviral active ingredients which intervene in viral replication in particular. This will be discussed in greater detail below.

An important general approach in the development of antiviral active ingredients and thus also in the prevention and/or treatment of virus-based diseases of the skin is thus to intervene in the viral replication cycle and to inhibit viral infection of the host cell or replication of the viral nucleic acid in the host cell, e.g., by inhibiting expression of the viral proteins coded by the viral nucleic acid.

In recent decades, such antiviral active ingredients, so-called virustatics have been developed. Many virustatics inhibit the enzyme DNA polymerase, reverse transcriptase or proteases, for example, and thus inhibit replication of the virus and/or processing of a synthesized long virus protein into smaller protein segments. Examples of these therapeutic approaches are to be found here in particular in the treatment of HIV infections. However, virustatics that are administered systemically or topically are also known in the field of treatment of virus-based diseases of the skin caused by herpesviruses HSV-1 or HSV-2. Examples include the active ingredients aciclovir, valaciclovir, foscarnet and penciclovir.

In general two approaches are known for prevent and/or treatment of virus-based diseases of the skin with virustatics:

(1) systemic administration: by systemic administration of virustatics, a significant reduction in the activation of viruses present in host cells can be achieved because the active ingredients inhibit the replication of the viral nucleic acid in the cell nucleus or the assembly of the viral particles to form complete viruses in the cytoplasm of the host cells;

(2) topical administration: by topical administration of virustatics in the area of an initial infection by the virus, the additional route of replication of the viruses, e.g., in the resulting fever blisters in the case of an HSV-1 infection, can be prevented in an early stage of activation, which can result in more rapid detumescence of the fever blisters.

Both approaches have some important disadvantages for administration of virustatics:

In systemic administration, the dose required for effective treatment is relatively high and is associated with serious adverse effects for the organism thereby treated such as, for example, nonspecific immune responses and autoimmune responses. In the case of aciclovir, numerous such adverse effects are known from the literature. Therefore, neither long-term treatment nor repeat treatment is advisable nor can it be expected of a patient.

In topical administration, the amount of active ingredient (virustatic) that can be released and be bioavailable per unit of time in the area of the virus infection, e.g., the fever blister is very low. This low bioavailability of the virustatic is an important obstacle for effective topical treatment. In the case of aciclovir which has a very low water solubility, the low bioavailability is due to the poor percutaneous transport of the active ingredient, for example. Various chemical modifications of virustatics as prodrug concepts for an improved supply of virustatic active ingredient have not led to any improvement in this phenomenon.

Of the virustatics described in the literature for treatment of virus-based diseases of the skin, aciclovir which has already been mentioned is described as one of the most effective virustatics for which there are almost no alternatives.

There are alternatives to the known antiviral active ingredients, in particular the virustatics, for prevention and/or treatment for virus-based diseases of the skin, which overcome the disadvantages known in the state of the art. There is therefore a need for developing improved and better tolerated antiviral active ingredients, which will intervene in the replication cycle of the virus and preferably inhibit (i.e., prevent) viral infection of the host cell and replication of the viral nucleic acid in the host cell.

BRIEF SUMMARY OF THE INVENTION

Thus the object of the present invention is to provide improved antiviral active ingredients for prevention and/or treatment of virus-based diseases of the skin.

This object is achieved through the present invention. The invention relates in its first two subjects to the use of deuterium oxide for prevention and/or treatment of virus-based diseases of the skin as well as the use of deuterium oxide for preparing a pharmaceutical drug for prevention and/or treatment of virus-based diseases of the skin.

BRIEF DESCRIPTION OF THE DRAWINGS

The present invention is also illustrated on the basis of FIG. 1 to 3, although these do not restrict the subject matters of the invention.

DETAILED DISCLOSURE OF THE INVENTION

Figure 1:
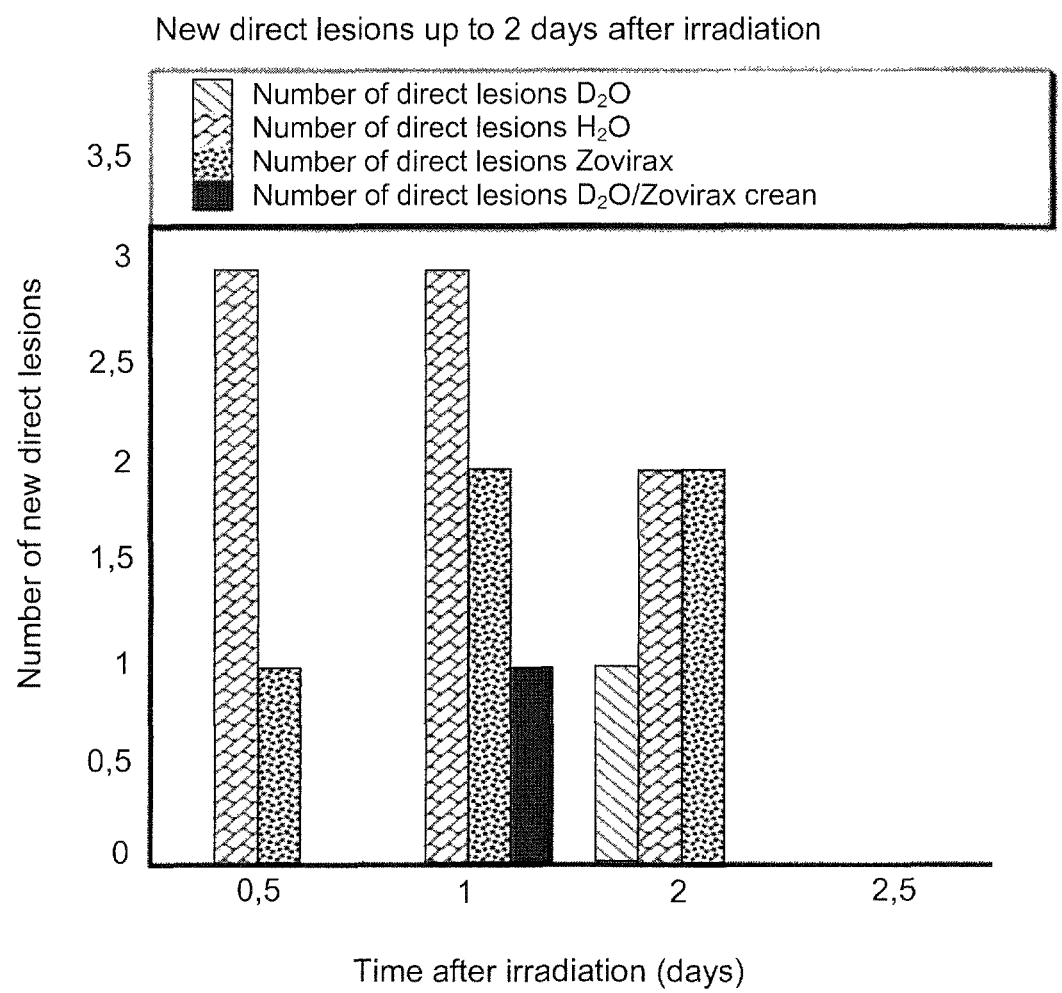
FIG. 1 shows a diagram of direct new lesions occurring up to two days after UV exposure. The number of direct new lesions in the period of time up to two days after UV radiation for four test groups of eight test subjects each, who were treated as follows beginning after UV exposure is shown: every 2.5 hours (except at night) the UV-exposed lip area of each of eight test subjects was treated by applying $D_2O$ carbopol acid gel (prepared with 100% $D_2O$ according to Example 1), with $H_2O$ carbopol acid gel (placebo prepared with 100 $H_2O$ according to Example 1), with Zovirax cream (aciclovir in a cream dispenser from GlaxoSmithKline) or with a $D_2O$ cream prepared according to Example 7 into which 20 wt % Zovirax cream had additionally been incorporated homogeneously.

In a preferred embodiment, the invention relates to the use of deuterium oxide for prevention and/or treatment of herpesvirus-based diseases of the skin. The herpesvirus-based diseases of the skin are preferably caused by herpes simplex virus type 1, herpes simplex virus type 2 or varicella zoster virus. These are especially preferably herpesvirus-based diseases of the skin selected from the group comprising herpes labiales, herpes nasalis, keratoconjunctivitis herpetica, stomatitis herpetica, herpes facialis, herpes buccalis, herpes genitales, herpes perianalis and herpes glutealis and herpes zoster.

In another preferred embodiment, the invention relates to the use of deuterium oxide for prevention and/or treatment of verrucal virus-based diseases of the skin. The verrucal virus-based diseases of the skin are preferably caused by papillomaviruses, in particular human papillomaviruses (HPV) or molluscipox virus. These are especially preferably verrucal virus-based disease of the skin selected from the group consisting of verrucae vulgares (common warts), verrucae planae juvenilis (juvenile (plane) warts), verrucae plantares (plantar warts), condylomata acuminata (venereal warts), verrucae planae (flat warts), verrucae filiformes (bristle warts) or molluscum contagiosum (dimple warts).

"Virus-based diseases of the skin" are understood to be diseases of the skin caused by a virus. The terms "virus-based disease," "viral disease" and "virus infection" of the skin are used as synonyms in the sense of the present invention. The term "herpesvirus-based diseases of the skin" is understood to refer to diseases of the skin caused by a herpesvirus. "Verrucal virus-based diseases of the skin" are understood to refer to diseases of the skin caused by a verruca virus. The verruca viruses include in particular papillomaviruses, especially human papillomaviruses (HPV) and molluscipox virus.

The terms "prevention and/or treatment" according to this invention refer to any measure suitable for treatment of a virus-based disease of the skin, which is either a preventive treatment of such a disease and/or symptoms thereof (prevention) or preventing a recurrence of such a disease, e.g., after a treatment period is concluded or treatment of the symptoms of such a disease that has already erupted (treatment).

Effective prevention or treatment of a virus-based disease of the skin may take place in particular by administering a pharmaceutical active ingredient and/or an antiviral active ingredient which preferably has all of the following properties, taking into account how it is administered (e.g., systemically or topically):

a) with antiviral active ingredients to be administered topically: a topical applicability by topical administration over a period of time of any length and with a high percutaneous transport kinetics of the active ingredient;

b) a largely homogeneous distribution of the active ingredient in the area of the site of action as well as preventing local excess concentrations;

c) a preferred enrichment of the antiviral active ingredient in the areas of skin infected by the virus, preferably in combination with retardation of its transdermal transport into the bloodstream, i.e., into the blood vessels;

d) a virustatic effect, i.e., an effect inhibiting the proliferation of viruses, on the (host) cells in the affected area skin, i.e., viral replication by the replication apparatus endogenous in the host cells is retarded, preferably inhibited;

e) extensive tolerance of the antiviral active ingredient due to the healthy (not infected by the virus) in the skin tissue and the bloodstream to prevent adverse effects, in particular with regard to immunological responses.

According to the present invention, it has been discovered that deuterium oxide ($D_2O$) meets the requirements listed above and also has some definite advantages over antiviral active ingredients, in particular virustatics, known in the prior art, e.g., it has a much lower incidence of adverse effects and/or none at all and has an increased bioavailability. It has also been found according to the present invention that deuterium oxide is an effective antiviral active ingredient with a potential long-term effect which is suitable for short-term, long-term and repeat treatment of virus-based diseases of the skin. According to the present invention, deuterium oxide, hereinafter referred to as $D_2O$, is also known as an antiviral active ingredient.

Before discussing details of deuterium oxide as an inventive antiviral active ingredient, the following explanatory definitions will be given.

The term "pharmaceutical active ingredient" is understood according to the present invention to refer to any organic or inorganic molecule, substance of compound having a pharmacological action. The term "pharmaceutical active ingredient" is used synonymously with the term "pharmaceutical drug" herein. The pharmaceutical active ingredients in the sense of the present invention also include antiviral active ingredients including $D_2O$.

The term "antiviral active ingredient" in the sense of the present invention defines an active ingredient which may be used for treatment of virus-based diseases and in particular virus-based diseases of the skin. Such an antiviral active ingredient is suitable in particular for inhibiting the viral infection of the host cell and/or replication of the viral nucleic acid in the host cell. If an antiviral active ingredient inhibits viral replication, the term "virustatic active ingredient" is also used.

"Cells" in the sense of the present invention are animal cells, preferably human cells, namely skin cells, in particular but not limited to epithelial cells of the skin such as mucosal cells and mucosal dermal cells. "Host cells" according to the present invention are skin cells that are or can be infected by a virus.

The properties of $D_2O$ and its mechanism of action as an inventive antiviral active ingredient are presented as follows.

Deuterium oxide ($D_2O$), which is frequently also referred to as "heavy water," is a substance that is very similar to "natural water" $H_2O$ in its physical properties. Deuterium oxide ($D_2O$) and water ($H_2O$) differ physically by the replacement of the hydrogen atoms of $H_2O$ by deuterium atoms, such that the density of $D_2O$ is approximately 10% higher than that of water and its viscosity is approximately 25% higher. In addition, the melting point and boiling point of $D_2O$ are higher than those of $H_2O$. A detailed comparison of properties can be found in the Handbook of Chemistry and Physics, section 6 by David R. Lide, editor, 79$^{th}$ edition, 1998 CRC Press, Boca Raton, USA.

In addition to the similar physical properties of $H_2O$ and $D_2O$, there are some important physiological differences (see also D. J. Kushner et al., Pharmacological uses and perspectives of heavy water and denatured compounds, Can J Physiol Pharmacol. 1999 February 77(2):79-88). Above a certain concentration in a cell, namely more than 20-25% in animal cells, $D_2O$ has an effect on enzymatic reactions. Enzymatically controlled reactions are increasingly altered, in particular being inhibited. One cause of this is seen as being the higher bonding strength of the hydrogen bridge bonds when the hydrogen atom of $H_2O$ is replaced by a deuterium atom. This increased bonding strength is manifested in aqueous solutions of $H_2O$ and $D_2O$ as well as in bonding of water to organic molecules (M. Cuma, S. Scheiner, Influence of Isotopic Substitution on Strength of Hydrogen Bonds of Common Organic Groups, Journal of Physical Organic Chemistry, 1997, vol. 10, 383-395).

It is general technical knowledge that a cell takes up different amounts of $H_2O$ depending on the degree of respective metabolic activity. A cell infected by a virus, a so-called host cell, in which replication of the virus is thus taking place will have a much higher metabolic activity than an uninfected cell of the same cell type as the surrounding tissue. The reason for this is that the host cell is responsible not only for its own replication but also for the replication of the virus. An increased metabolic activity of cells correlates with an increased water uptake, so virus-infected host cells take up much more water ($H_2O$) than uninfected cells. Due to the similar physical properties of $H_2O$ and $D_2O$, $D_2O$ is taken up by cells in parallel with $H_2O$ (if $D_2O$ and $H_2O$ are available) or instead of $H_2O$ (if only $D_2O$ is available).

As explained above, enzymatic reactions in the cell are altered by $D_2O$ in sufficient concentration. As already explained, cells, and virus-infected cells to an increased extent, take up $D_2O$ in parallel with or instead of $H_2O$. Thus, when $D_2O$ is administered to a virus-infected cell in an "adequate concentration" according to the present invention, i.e., more than 20% based on the total water content of a cell, then this has an inhibiting effect on the enzymatic reactions in the host cell. This includes in particular inhibition of DNA polymerase (H. Takeda et al., Mechanisms of cytotoxic effects of heavy water (deuterium oxide: $D_2O$) on cancer cells, Anticancer Drugs, 1998 September; 9(8):715-25). As a result, DNA replication in a cell is inhibited. Uninfected cells in the surrounding tissue take up $D_2O$ and/or $H_2O$ to a normal extent, so there is no inhibition of enzymatic reactions in these cells.

According to the present invention, it has now been found that when a cell is infected with a virus (host cell), the viral DNA is also not replicated due to inhibition of the endogenous DNA polymerase of the host cell because its replication also takes place through the host cell DNA polymerase. In the case of RNA viruses, there is also enzymatic inhibition by $D_2O$ for synthesis of reverse transcriptase, which must first be synthesized in the host cell, coded by viral genes, to transcribe the viral RNA into DNA, which is then in turn replicated by the DNA polymerase of the host cell. Thus when certain enzymatic reactions of the host cell are inhibited by $D_2O$, this also inhibits and/or prevents viral replication.

Another important aspect of the present invention, which is based on the increased bonding property of $D_2O$ described here, is that when $D_2O$ is administered in a sufficient concentration, i.e., more than 20% in a cell, mitosis is inhibited or prevented. In all probability this takes place in addition to the aforementioned inhibition of DNA replication due to the inhibition of mitosis in the cycle of mitosis of animal cells (J. A. Laissue et al., Survival of tumor-bearing mice exposed to heavy water or heavy water plus methotrexate, Cancer Research, 1982, vol. 42(3): 1125-1129). According to the present invention, this is of crucial importance for a latency condition in virus-based diseases of the skin, in which viruses are in the dormant state (latency) already described above during the lysogenic replication cycle. In this state, the viral genome is integrated into the host cell genome and is transmitted together with the host genome to the host cell progeny in mitosis of the host cell. When mitosis is inhibited, the transmission of the virus to new cells is thus prevented.

According to the present invention, viral replication is thus inhibited by using $D_2O$ for prevention and/or treatment of virus-based diseases of the skin. According to the present invention, this inhibition of viral replication by $D_2O$ as an antiviral active ingredient takes place in particular by inhibiting replication of the viral nucleic acid and/or host cell mitosis.

The terms "inhibit" and/or "inhibition" according to the present invention are understood to mean that the replication of viral nucleic acids and/or the cell mitosis rate of host cells according to the present invention is/are delayed and/or reduced, preferably up to approximately 5%, especially up to approximately 10%, also preferably up to approximately 20%, more preferably up to approximately 30%, also more preferably up to approximately 40%, even more preferably up to approximately 50%, most preferably up to approximately 60% in comparison with the replication and/or mitosis rate of these cells or the viral replication rate without administration of $D_2O$.

The term "inhibit" or "inhibition" according to the present invention means that the replication of viral nucleic acids and/or the cell mitosis rate of host cells according to the present invention is delayed or reduced by preferably more than 50%, also preferably up to approximately 60%, more preferably up to approximately 65%, especially up to approximately 70%, also preferably up to approximately 80%, more preferably up to approximately 90%, also more preferably up to approximately 95%, even more preferably up to approximately 98%, most preferably up to 100% in comparison with the replication rate and/or mitosis rate of these cells or the viral replication rate without administration of $D_2O$.

Such an antiviral and/or virustatic effect of $D_2O$ has not previously been described or indicated in the prior art.

$D_2O$ has considerable advantages in comparison with the known antiviral and/or virustatic active ingredients for treatment of virus-based diseases of the skin, especially due to the following properties:

1) Due to the possibility of applying $D_2O$ topically to the skin, a sufficiently high concentration for therapeutic efficacy (more than 20%, based on the total water content of a cell) of $D_2O$ can be achieved in the dermis and/or epidermis of the skin because of the high cutaneous, percutaneous and intracutaneous transport of $D_2O$ into this skin cells without exposing other organs of the body to similarly high concentration, possibly dangerous concentrations of $D_2O$, which may be the case in systemic administration. This solves an important problem which is discussed in the prior art for achieving therapeutically effective $D_2O$ concentrations at the site of action (more than 20% $D_2O$, based on the total water content of the cell) without severe adverse effects for other organs or healthy surrounding skin tissue. The basis for this is the directed transport of $D_2O$ through the stratum corneum of the skin to the epidermis or dermis;

2) The physical state of $D_2O$ may be liquid, gaseous or solid in topical administration. Transport into the skin may be accomplished by direct contact of $D_2O$ and/or a $D_2O$-containing formulation with the skin and indirectly by diffusion through an intermediate layer (e.g., air, porous membrane, polymer network);

3) In the case when pure liquid $D_2O$ is administered alone (pure $D_2O$), it should be pointed out that $D_2O$ has a unique advantage in comparison with all other liquid pharmaceutical active ingredients. It can be transported into the skin like normal water ($H_2O$), and furthermore, the depth of penetration of $D_2O$ into the skin can be adapted to the therapeutic goal through the strength and direction of the osmotic gradient and by manipulation of these two variables;

4) The hydrogen bridge bonding strength of $D_2O$ is greater than that of $H_2O$, as already described above, in particular in binding of water to organic molecules. Topically administered $D_2O$ forms molecular bonds by forming hydrogen bridge bonds to the nearest available cell surface and thereby displaces the $H_2O$ attached there on the basis of its higher bonding strength. The exchange frequency of $D_2O$ molecules with the $H_2O$ environment is in turn somewhat slower due to this increased bonding strength (and due to the higher weight of the $D_2O$ molecule) than for $H_2O$ (S. König et al., "Molecular dynamics of water in oriented multilayers studied by quasielastic neutron scattering and deuterium NMR relaxation", 1994, J. Chem. Phys. 100, 3307-3316). This yields an increased probability of retention of $D_2O$ molecules directly on the cell surface combined with an increased internalization of $D_2O$ in the cell so that it can manifest its effect—inhibition of the enzymatic reactions of a virus-infected host cell and mitosis thereof as described above. Since virus-infected skin cells have a higher uptake capacity for water and/or $D_2O$ than do normal cells, this also ensures that $D_2O$ will be superproportionally enriched in the cells in comparison with healthy skin cells, i.e., in an adequate $D_2O$ concentration of more than 20%, based on the total water content of the cell. On the basis of these properties, topical application of $D_2O$ to the skin is extremely valuable for treatment of virus-based diseases of the skin in which the site of action is in the epidermis or at most in the dermis of the skin;

5) $D_2O$ is the only nonradioactive molecule that greatly resembles $H_2O$ in its properties. Cells in general and skin cells in particular cannot "differentiate" between the two molecules so that $D_2O$ is transported by active and passive transport into the cell in the same way as $H_2O$ and even enters the cell nuclei. In this way cell barriers of any type which prevent penetration of other pharmaceutical active ingredients are bypassed and also defense mechanisms on a cellular level such as internalization in lysosomes or activation of MDR (multiple drug resistance) transporters or on an organ level by the immune system which can reduce or inhibit the efficacy of the pharmaceutical active ingredient $D_2O$ are largely eliminated 6) Another advantage of $D_2O$ as an antiviral and/or virustatic active ingredient is the fact that the concentration of less than 20% $D_2O$ (based on the total water content of the cell) does not manifest any significant effects in the cell and thus normal cells which take up comparatively little $D_2O$ because of their lower water permeability and/or water uptake capacity in comparison with the active virus-infected cells, are hardly exposed to the effects of $D_2O$.

In an especially preferred embodiment of the present invention, $D_2O$ is not administered systemically according to the present invention but instead is administered nonsystemically, in particular topically. This avoids in particular adverse effects that are caused by systemic administration of antiviral and/or virustatic active ingredients.

Through an inventive topical administration, high local therapeutically active $D_2O$ concentrations on the skin may be used and at the same time the burdens to the system (i.e., the bloodstream) and the adverse effects on healthy skin tissue that is not to be treated and tissue of other organs (e.g., the liver or kidneys which could be caused by a high concentration of $D_2O$ of more than 20% $D_2O$, based on the total water content of the cell) can be reduced and/or completely prevented. Transport of $D_2O$ from the skin cells into the system can also be prevented or restricted with agents that are well known in the prior art. Examples of these agents include, e.g., targeted manipulation of the osmotic gradient over the skin (i.e., between the systemic part and the skin surface) by reducing the water potential of the topically applied $D_2O$ by means of substances suitable for altering this water potential, in particular physiologically tolerable salts such as sodium chloride, water-soluble polymers and other non-pharmaceutical substances.

The term "topical" and/or "topical application" or "topical administration" or "topical use" in this sense of the present invention refer to the local application or introduction of $D_2O$ and other inventive active ingredients, e.g., pharmaceutical active ingredients or non-pharmaceutical active ingredients to the skin, preferably as a liquid, gas or formulation, in particular as an ointment, cream, gel or hydrogel.

An inventive topical administration is preferably accomplished by Administration as a liquid or formulation, in particular as an ointment, cream or gel (described in greater detail below);

1) Administration via a patch or a bandage (described in greater detail below) or 2) Administration as an aerosol or vapor (described in greater detail below).

An organism to be treated in the sense of the present invention is an animal organism, especially a vertebrate, in particular a mammal, especially a human, horse, swine, cattle, goat, sheep, cat and/or dog.

$D_2O$ may be administered according to this invention solely as a pharmaceutical active ingredient, more specifically as an antiviral and/or virustatic active ingredient, or in combination with another pharmaceutical active ingredient or with another non-pharmaceutical active ingredient (in particular for optimization of topical application of $D_2O$ as a pharmaceutical active ingredient to the skin).

A preferred embodiment of the present invention relates to the inventive use of $D_2O$, whereby the $D_2O$ is used together with at least one other pharmaceutical active ingredient and/or at least one other non-pharmaceutical active ingredient.

Such a combination of $D_2O$ and at least one other pharmaceutical active ingredient and/or at least one other non-pharmaceutical active ingredient is referred to below as the "inventive combination."

All the inventive applications and administrations of $D_2O$ disclosed in this description, e.g., with patches and bandages, with layered systems, in formulations and as an aerosol are also applicable to an inventive combination without restriction unless otherwise stated to the contrary. The same thing is also true for the use and administration of $D_2O$ in combination with $HH_2O$, also referred to below as "mixture of $D_2O$ and $H_2O$."

Another preferred embodiment of the present invention relates to the use of $D_2O$ together with at least one other pharmaceutical active ingredient, whereby the latter is selected from the group consisting of virustatics, proteins, peptides, nucleic acids and immunosuppressant active ingredients.

Additional pharmaceutical active ingredients of an inventive combination, as well as the use thereof, which are preferred according to the present invention are listed below, but this list is intended only an example and the present invention is not limited thereto:

Virustatics
  Virustatics are active ingredients which inhibit the replication of viruses. Numerous virustatics inhibit the activity of enzymes, for example, DNA polymerase, reverse transcriptase or proteases, and thus inhibit the replication of the virus and/or processing of the synthesized long virus protein into small protein segments. Examples of virustatics include aciclovir, valaciclovir, foscarnet and peniclovir.
Immunosuppressant active ingredients
  By adding immunosuppressant active ingredients, e.g., corticoids and/or others or immunomodulators, it is possible to improve and optimize the reaction of the skin tissue to replication of the viruses, in particular when there are pre-existing inflammations.
Proteins
  Proteins that may be used according to the present invention are understood to include proteins which intervene in the replication mechanism of the host cell in a suitable manner. "In a suitable manner" in this context means that the proteins inhibit adsorption of the virus onto the host cell, injection of viral nucleic acid into the host cell, replication of the DNA of the host cell and/or the nucleic acid of the virus, processing of the viral nucleic acid or assembly of the viral particles to form the complete virus; they preferably inhibit or otherwise intervene in the replication cycle of the virus. Examples of this include protease inhibitors, uncoating inhibitors, penetration inhibitors, reverse transcription inhibitors and DNA polymerase inhibitors.
Peptides
  Peptides usable according to the present invention are understood to be, for example, peptides which influence the membrane permeability of the host cell membrane in a suitable manner, in particular by increasing it. In this way, an improved transport of $D_2O$ and optionally the additional pharmaceutical or non-pharmaceutical active ingredients according to the present invention into the host cell can be achieved. Mellitin is one example of this.
Nucleic acids
  By adding nucleic acids, a change in the genetic information of the cells in the area of the active site or a targeted elimination ("gene silencing") of certain genes, e.g., DNA polymerase of cells in the area of the site of action within the skin tissue can be achieved in parallel with the antiviral and virustatic effect of $D_2O$ and thereby a modification of the proteoma may be achieved. For example, gene silencing may lead to elimination of the genes involved in defense against DNA damage (e.g., p53, BRCA1, BRCA2, ATM, CHK2) and therefore the viruses in the cells that are prevented from replicated by $D_2O$ can no longer return to a latent stage even in the long run (after the end of topical administration of $D_2O$) but instead are hindered from expression of viral DNA in the long run. Those skilled in the art are well aware of methods of performing "gene silencing" as described for example by C. C. Mello, D. Conte: "Revealing the world of RNA interference" in Nature 431, 338-342 (Sep. 16, 2004). The nucleic acids are preferably DNA, especially oligonucleotides, sense or antisense DNA, natural or synthetic, cDNA, genomic DNA, naked DNA, single-stranded or double-stranded DNA or circular DNA or RNA, preferably antisense RNA, RNAi, siRNA or other RNA molecules that are suitable for interference and are not limited in the length.

The concentration of additional pharmaceutical active ingredients used in addition to $D_2O$ as active pharmaceutical ingredients according to the present invention, based on the total solution of an inventive combination, is in the range from at least $10^{-8}$ M to at least $5 \cdot 10^{-2}$ M, preferably at least $10^{-7}$ M to $10^{-3}$ M, most preferably at least $10^{-6}$ M to at least $10^{-2}$ M. An especially preferred concentration range is in the range of at least $10^{-9}$ M to at least $10^{-2}$ M.

Another preferred embodiment of the present invention relates to the use of $D_2O$ together with at least one additional non-pharmaceutical active ingredient, whereby the latter is selected from the group comprising pharmaceutically tolerable organic or inorganic acids or bases, polymers, copolymers, block copolymers, simple sugars, complex sugars, ionic and nonionic surfactants or lipids as well as mixtures thereof, albumin, transferrin and DNA repair proteins such as kinase inhibitors.

The term "non-pharmaceutical active ingredient" in the sense of the present invention refers to any pharmacologically tolerable and therapeutically appropriate molecule, substance or compound that is not a pharmaceutical active ingredient but is administered to an organism that is to be treated, preferably together with at least one inventive pharmaceutical active ingredient, e.g., formulated in an inventive formulation to influence qualitative properties of the pharmaceutical active ingredient(s) in particular to improve them. The non-pharmaceutical active ingredients preferably do not manifest any pharmacological effect or no mentionable or at least no adverse pharmacological effect with regard to the intended prevention or treatment of virus-based diseases of the skin. Suitable non-pharmaceutical active ingredients include for example pharmacologically safe salts, e.g., sodium chloride, flavorings, vitamins, e.g., vitamin A or vitamin E, tocopherols or similar vitamins or provitamins that occur in the human body, antioxidants, e.g., ascorbic acid as well as stabilizers and/or preservatives for prolonging the use time and/or storage time of a pharmaceutical active ingredient or a inventive formulation and other conventional non-pharmaceutical active ingredients and/or excipients and additives with which those skilled in the art are familiar. Additional non-pharmaceutical active ingredients preferred according to the present invention include in particular all substances capable of forming aqueous gels such as natural or synthetic water-soluble polymers capable of forming networks.

Additional non-pharmaceutical active ingredients of an inventive combination preferred according to the present invention and their effect as well as suitable concentrations are given below, but this list is intended only as an example and the present invention is not limited thereto:

Water-soluble excipients and additives

By adding water-soluble excipients and additives, e.g., pharmaceutically tolerable organic or inorganic acids, bases, salts and/or buffer substances to adjust the pH, the physiological tolerability of the $D_2O$ in and on the skin for non-virus-infected cells can be improved.

Examples of preferred inorganic acids are selected from the group comprising hydrochloric acid, hydrobromic acid, nitric acid, sulfuric acid and phosphoric acid, but hydrochloric acid and sulfuric acid are especially preferred. Examples of especially suitable organic acids are selected from the group comprising maleic acid, tartaric acid, maleic acid, succinic acid, acetic acid, formic acid and propionic acid and especially preferably ascorbic acid, fumaric acid and citric acid. If necessary, mixtures of the aforementioned acids may also be used, in particular acids which also have other properties in addition to their acidification properties, e.g., when used as antioxidants, e.g., citric acid or ascorbic acid. Examples of pharmaceutically tolerable bases include alkali hydroxides, alkali carbonates and alkali ions, preferably sodium. Mixtures of these substances may be used in particular to adjust and buffer the pH, with potassium hydrogen phosphate and dipotassium hydrogen phosphate as well as sodium hydrogen phosphate and disodium hydrogen phosphate being especially preferred. Preferred buffer substances in the sense of the present invention also include PBS, HEPES, TRIS, MOPS and other physiologically tolerable substances with a pK value in the range of 5.0 to 9.0. The concentration of these substances, based on the total solution of an inventive combination, is preferably in the range from micromolar to millimolar, especially preferably in the range of 1-100 mM.

Water-soluble polymer molecules

By adding water-soluble noncytotoxic molecules, e.g., certain polymers (e.g., but not limited to these, dextran, polyethylene glycol, agarose, cellulose, acrylic acid, hyaluronic acid), copolymers and block copolymers, an additional delay (retardation) in the transition of $D_2O$ from topical application forms into the skin as well as from the skin into the system can be achieved due to their high water binding capacity. Furthermore, due to the ability of polymers to reduce the chemical potential (water potential) of $D_2O$, the strength and direction of the osmotic gradient over the skin can also be altered and/or improved and optimized. The concentration of these substances, based on the total solution, is in the range from micromolar to molar, preferably in the range of 1-500 mM.

Water-soluble nonpolymer molecules

Due to the addition of water-soluble nonpolymer molecules which alter the density and/or viscosity of $D_2O$, e.g., simple sugars and complex sugars, in particular glucose, sucrose, dextrose, maltose, starch and cellulose, but not limited thereto, the osmotic conditions in the area of topical $D_2O$ application and $D_2O$ transport and $D_2O$ retention in the skin can be altered and/or optimized. The concentration of these substances, based on the total solution of an inventive combination, is preferably in the range from millimolar to molar, especially preferably in the range of 1.0 mM to 1.5M.

Molecules that alter the $D_2O$ interfacial tension

By adding substances which alter the interfacial tension of $D_2O$, for example, ionic and nonionic surfactants or lipids, in particular a mixture of surfactants and lipids, but not limited thereto, the transport of $D_2O$ from the topical application into the skin and also within the skin can be altered. The concentration of these substances, based on the total solution of an inventive combination, is preferably in the range from micromolar to millimolar, especially preferably in the range of 0.5-500 mM.

Water-soluble noncytotoxic molecules

By adding water-soluble molecules which are known to be taken up by cells that are especially active metabolically, e.g., virus-infected cells to a particular extent, e.g., albumin or transferrin, it is possible to achieve an additional increase in the rate of $D_2O$ transport of the molecules surrounded by a $D_2O$ hydrate shell into the target cells in the skin.

The concentration and/or dosage of $D_2O$ and optionally the at least one additional pharmaceutical and/or non-pharmaceutical active ingredient is subject to various factors, e.g., the type of treatment, the type of disease, the disease state of the patient (mammal), the type of active ingredient, etc. Those skilled in the art are aware of such parameters and the determination of the specific doses is subject to the technical expertise of those skilled in the art. Suitable concentration data are disclosed herein. Some example of information on suitable concentration ranges are already given above but these merely be guideline values.

The $D_2O$ that can be used according to the present invention is preferably in the form of a liquid. The $D_2O$ is preferably in a solution, especially with $H_2O$ (water) as the solvent, and is also referred to herein as a "mixture of $D_2O$ and $H_2O$" or "$D_2O/H_2O$" when $H_2O$ is present and/or as a "$D_2O$ solution" or "pure $D_2O$" if no $H_2O$ is present. Pure $D_2O$ contains $D_2O$ preferably in a concentration range from 98.1% to 100%, especially from 98.5% to 99.9%, especially preferably from 99.7%, based on the total water content of the solution. An inventive mixture of $D_2O$ and $H_2O$ preferably contains $D_2O$ in a concentration range from 1% to 98%, preferably 5% to 95%, more preferably from 10% to 90%, also preferably from 15% to 80%, more preferably from 20% to 70%, also more preferably from 30% to 60%, most preferably from 40% to 50%, whereby these amounts are based on the total water content of the mixture of $D_2O$ and $H_2O$. Production of an inventive $D_2O$ solution and, by analogy thereto, an inventive combination takes places, e.g., by mixing the component, in particular $D_2O$ and optionally $H_2O$ plus optionally the at least one additional pharmaceutical and/or non-pharmaceutical active ingredient. In addition, if necessary a solvent may be added by mixing as described below. The admixture of $H_2O$ and/or the at least one additional pharmaceutical and/or non-pharmaceutical active ingredient and/or the solvent to $D_2O$ preferably takes place in the liquid physical state. However, the preparation may be achieved through any suitable method. In the case when $D_2O$ is used alone (i.e., not in combination with other pharmaceutical active ingredients and/or non-pharmaceutical active ingredients) and at a concentration of 100% and/or approximately 99.9%, based on the total volume of the solution (i.e., pure $D_2O$), then pure $D_2O$ is the inventive $D_2O$ solution.

All the inventive uses and (topical) applications of $D_2O$ disclosed in this description are also applicable without restriction to an inventive mixture of $D_2O$ and $H_2O$ unless otherwise indicated to the contrary. Likewise, applications of an inventive mixture of $D_2O$ and $H_2O$ may be used to an unlimited extent, unless indicated to the contrary, with respect to the inventive combinations, layer systems, patches and bandages, formulations and aerosols (see below).

The inventive use of $D_2O$ may also be accomplished as an aerosol, vapor or formulation, in particular as a cream, ointment or gel, in particular a hydrogel, as described in greater detail below. The concentrations of $D_2O$ to be used in this context are also discussed in detail below.

In a preferred embodiment, the at least one additional pharmaceutical active ingredient and/or additional non-pharmaceutical active ingredient is bound to $D_2O$.

"Bound" in the sense of the present invention means that the pharmaceutical active ingredient and/or the non-pharmaceutical active ingredient is/are hydrated by the $D_2O$.

In other preferred embodiments, the $D_2O$ and/or the inventive combination is/are present in a suitable solvent. An inventive solvent may be an organic or inorganic solvent. Suitable solvents according to the present invention should preferably be tolerated well physiologically by the organism (in particular mammal), to which the active ingredient is administered with the solvent, i.e., should not cause any adverse effects, e.g., toxic adverse effects. An especially preferred solvent is distilled water. Ethanol-water mixtures are also preferred. The percentage amount of ethanol by weight in these mixtures is preferably in a range between 5% and 99% ethanol, also preferably in a range from 10% to 96% ethanol, more preferably between 50% and 92%, most preferably between 69% and 91% ethanol.

$D_2O$ or an inventive combination may be used in a "pre-formulated" form, e.g., packaged in suitable agents for transport of pharmaceutical active ingredients, so-called drug delivery systems, e.g., in nanoparticles, vectors, preferably gene transfer vectors, viral or nonviral vectors, poly- or lipoplex vectors, liposomes or hollow colloids (i.e., hollow spheres of colloidal dimension). Also suitable for transport are naked nucleic acids, in particular naked DNA. Suitable vectors, liposomes, hollow colloids or nanoparticles as well as methods of introducing substances into such vectors, liposomes, hollow colloids or nanoparticles are well known in general in the prior art and are described, for example, by S. A. Cryan, Carrier-based strategies for targeting protein and peptide drugs to the lungs, AAPS Journal, 2005, 07(01):E20-E41 and Sambrook et al., Molecular Cloning A Laboratory Manual, Cold Spring Harbor Laboratory (1989), New York. Preferably polyethylenimine or cationic lipids, e.g., DOTAP may be used as the gene transfer vectors. Liposomes are preferably used for packaging of cytostatics; a detailed description is given, for example, by N. V. Koshkina et al., N. V. Koshkina et al. [sic], Paclitacel liposome aerosol treatment induces inhibition of pulmonary metastases in murine carcinoma model, Clinical Cancer Research, 2001, 7, 3258-3262. Proteins as pharmaceutical active ingredients may preferably be packaged by means of supercritical liquids, emulsion methods and spray drying in biocompatible polylactic acid/glycolic acid polymers (PLGA).

Topical administration of $D_2O$ may also be performed by using a patch or a bandage. Another preferred embodiment thus relates to the inventive use of $D_2O$, whereby $D_2O$ is applied topically with a patch and/or via a patch or a bandage.

A "patch" or "bandage" in the sense of the present invention is understood to include all devices that can be attached to the skin by mechanical or chemical interaction, physisorption, adhesion or other physicochemical processes and are suitable for covering a selected area of skin occlusively or nonocclusively over a period of time long enough by the intended treatment and allowing and/or supporting a supply of $D_2O$ to the skin. Patches and bandages that are usable according to the present invention as administration systems for local release of active ingredients on the skin (e.g., heat patches) and for controlled systemic release of active ingredients (e.g., opiate depot patches, nitroglycerin depot patches) are known in the prior art. A "depot patch" or "depot bandage" is also understood to include the ability of the patch or the bandage to store $D_2O$ and release it in a controlled manner to the skin over a period of days or weeks in addition to the properties described above. Such depot patches and/or depot bandages are covered by the terms patch and/or bandage as used below.

On the whole, the following problem must be taken into account for any controlled release of $D_2O$ to the skin: release from a liquid or formulation as an ointment, cream or gel applied directly to the skin may be made more difficult due to the direction of the osmotic gradient within the skin from the inside to the outside because the $D_2O$ in the liquid, ointment, cream or gel under some circumstances has a lower water potential than the $H_2O$ in the skin and in the vessels beneath that.

Therefore, an especially preferred embodiment of topical application of $D_2O$ is to regulate and thus control the depth and/or degree of penetration of $D_2O$ into the skin through a targeted manipulation of the osmotic conditions in the area of skin to be treated, preferably controlling its penetration to the depth at which the hyperproliferating cells are located, especially to the epidermis or to the dermis. This may be achieved through the selected composition of an applied inventive combination by adding substances which are capable of altering the osmotic conditions at the surface of the skin. Examples of such substances are given above.

Another possibility of controlling the penetration of $D_2O$ into the skin is to use one or more membranes or films which allow the passage of water and gases that prevent the passage of larger molecules or particles (including bacteria, viruses, single cell organisms). Examples of such membranes and films usable according to the present invention are known in the prior art and have numerous applications, e.g., in textiles under the brand names Gore-Tex® or so-called biofilms in medicine or respiratory active patches such as Tegaderm®.

An especially preferred embodiment of the invention therefore consists of the inventive use of $D_2O$, whereby $D_2O$ is applied topically with a patch or bandage, the patch or bandage being used in combination with at least one membrane or at least one film. The at least one membrane and/or the at least one film is preferably a microporous or nanoporous membrane and/or film.

In an especially preferred embodiment, the inventive topical use of $D_2O$ is accomplished via a special arrangement. This arrangement consists of the following components:
- a microporous or nanoporous membrane or film which is applied directly to the skin, as described above,
- followed by a $D_2O$ layer which contains the $D_2O$,
- optionally followed by a so-called occlusive layer that prevents evaporation of the $D_2O$ to the outside or regulates it and at the same time forms a mechanical protection which prevents the escape of $D_2O$ as a liquid, and
- followed by a patch or a bandage.

In another preferred embodiment, the inventive topical use of $D_2O$ is accomplished via another special arrangement. This arrangement consists of the following components:
- a microporous or nanoporous membrane or film which is applied directly to the skin, as described above,
- followed by a $D_2O$ layer which contains the $D_2O$,
- optionally follows by a so-called occlusive layer which prevents evaporation of the $D_2O$ to the outside or regulates it and at the same time forms a mechanical protection which prevents the escape of $D_2O$ as a liquid, and
- followed by another microporous or nanoporous membrane or film as described above.

If needed, additional $D_2O$ layers containing additional $D_2O$ and separated from membranes and/or films may of course also be added, thereby altering the depot effect or the transfer of the $D_2O$ into the skin, e.g., varying the amount and/or duration of the release of $D_2O$. The term "$D_2O$ layer" as used here refers to a pure liquid $D_2O$, a mixture of $D_2O$ and $H_2O$ and a formulation of $D_2O$, in particular as a cream, ointment, gel or hydrogel.

Likewise layers having chemical, electrical or thermal properties which are suitable for manipulating the transfer of $D_2O$ into the skin and/or the duration of its release may preferably also be added. Examples include layers that are suitable for creating and/or maintaining an electric, thermoelectric, thermal or chemical potential (or a combination thereof) over the underlying layers and the skin. This may be accomplished, for example, by electrodes embedded in the membranes or films described here or situated on them, said electrodes being supplied with electric current from the outside (direct voltage, alternating voltage or high frequency currents) or generating electrochemical potentials through a targeted choice of the electrode material with the $D_2O$ layer as the electrolyte.

The totality of such $D_2O$ layers, occlusive layers, layers with chemical, electrical or thermal properties, membranes and films in any number, combination and arrangement suitable for the intended purpose, as described, above is referred to below as the "layer system." Such a layer system is preferably used in combination with a (depot) patch or (depot) bandage as described above.

By varying the morphology (pore size, membrane and/or film thickness, surface roughness and surface profile) and surface properties (e.g., hydrophilic or hydrophobic, chemical coatings covalently bonded or adhesively bonded, functional groups, binding without incorporation of inorganic or organic substances), the membrane or film which is in direct contact with the skin, the transfer of $D_2O$ from a patch, bandage or layer system as described here into the skin can be influenced and/or varied in a targeted manner in this way.

Another variation of the entrance of $D_2O$ into the skin is possible through targeted use of adhesives which may be used for mechanical attachment of the (depot) patch or the (depot) bandage to the skin but are not necessary. The adhesives generally used for topical application of patches and bandages tend to have a hydrophobic character, which can prevent the passage of $D_2O$ through the adhesive layer. By adding additives to the adhesive preparation, a change in these properties can be achieved. Such "additives" include organic and/or inorganic substances and compounds which are capable of altering the permeation properties of $D_2O$ through the adhesive layers. Examples of such substances include polymers, copolymers, block polymers, block copolymer, surfactants, peptides, proteins, nucleic acids, sterols and steroids.

In another preferred embodiment, the inventive use of $D_2O$, preferably with a patch or a bandage, topically to the skin is accomplished via an arrangement which allows the transfer of $D_2O$ into the skin largely or exclusively via the vapor phase. In other words, $D_2O$ used as a liquid according to the present invention evaporates as molecular $D_2O$ and comes in contact with the skin as a vapor. The $D_2O$ concentrations thus correspond to the concentrations of a liquid containing $D_2O$ as described above. $D_2O$ in vapor form has the advantage of penetrating especially easily into the skin. To achieve this evaporation, thermal energy is required and may be obtained either from the skin itself or from an external heat source, e.g., an electric heater (e.g., Peltier heating) introduced into the patch or bandage when using a patch or bandage as described here or the layer system described above. In addition to this thermal energy, through targeted modifications, e.g., the choice of the morphology (in particular the pore size and surface coating) of a first membrane or film of the layer system described above as being applied to the skin, it is possible to achieve the effect that only $D_2O$ in vapor form can penetrate through the membrane or film as far as the skin, whereas liquid $D_2O$ is retained. With this embodiment, the amount and duration of release of $D_2O$ through the vapor phase can be controlled and/or varied through the changes in the layer system and corresponding modifications in additional membranes or films that are optionally used as described above.

Another preferred embodiment of the invention relates to the use of $D_2O$, where $D_2O$ is applied topically as an aerosol.

The term "aerosol" is understood to refer to solid or suspended particles having a diameter of approximately 0.0001 μm to approximately 100 μm in gases, in particular air, whereby the composition and form of the aerosols may vary greatly. The smallest pharmaceutically active particles in aerosols are nucleic acids, peptides or proteins, for example, while the largest particles are fog particles, for example. Aerosols frequently consist of mixtures of particles of different particle sizes and thus embody a polydisperse size distribution. Aerosols can be prepared artificially through dispersion and condensation methods that are well known in the prior art. These methods may be used without a propellant gas or may be used in combination with a liquefied pressurized gas as the propellant, e.g., in spray cans.

The inventive use of $D_2O$ as an aerosol is preferably accomplished by using an atomizer. An "atomizer" for the present invention is any apparatus found to be suitable for medicinal aerosols, with which aerosol particles in the size range of 50 nm to 50 μm can be produced. The atomizer sprays a defined volume of $D_2O$, usually employing high pressures, through small nozzles to thereby create an aerosol that can be applied to the skin.

Suitable atomizers for [the present invention][1] also include inhalers or atomizers driven by propellant gas. Propellant gases for this purpose may be, for example, chlorofluorohydrocarbons CFHC or halogenated fluorohydrocarbons HFHC. In this regard, reference is made to "Theory and Practice of Inhalation Therapy," pages 31 to 70, Arcis Verlag (2000), where detailed description of atomizers that can be used as well as methods of using them can be found.

Examples of atomizers suitable according to the present invention include compressed air-driven nozzle atomizers (e.g., PARI LC plus, PARI GmbH, Starnberg, Germany), Venturi nozzle atomizers, water vapor-driven nozzle atomizers or ultrasonic atomizers (e.g., AeronebLab, Aerogen, Inc., Stierlin Court, Canada; eFLOW, PARI GmbH, Starnberg, Germany). Atomizers of a size that allows them to be carried by the patient (person), e.g., the Respimat@ [sic; Respimat®] as described in WO 97/12687 are also suitable. All the references cited here are fully included in the present invention.

Production of an aerosol that can be used according to the present invention may take place on the basis of suitable known standard techniques for production of an aerosol.

The $D_2O$ concentrations to be used for the use of $D_2O$ as an aerosol according to the present invention depends on various factors, e.g., the intended purpose, the disease condition, and are subject to the technical expertise of those skilled in the art. An aerosol that can be used according to the present invention contains $D_2O$ preferably in a concentration range from 1 wt % to 98 wt %, preferably 10 wt % to 90 wt %, also preferably from 15 wt % to 80 wt %, more preferably from 20 wt % to 70 wt %, also more preferably from 30 wt % to 60 wt %, most preferably from 40 wt % to 50 wt %.

The administration as an aerosol for the inventive use of $D_2O$ is preferably administered directly to the skin in the area to be treated. This may be accomplished, e.g., by a chamber which can be placed on the skin and is open toward the skin and through which the aerosol is passed.

Another preferred embodiment relates to the inventive use of $D_2O$, where $D_2O$ is applied topically as a formulation. Such a formulation is preferably an ointment, cream or gel, in particular a hydrogel.

The term "ointment" according to the present invention is understood to refer to a pharmaceutical drug preparation to be applied externally consisting of a basic composition of spreadable substances such as liquid petrolatum to which the actual pharmaceutical and/or non-pharmaceutical active ingredients are added, e.g., by mixing.

The term "cream" in the sense of the present invention is understood to refer to an inventive ointment which may additionally contain other ingredients such as cosmetic active ingredients, e.g., perfumes, coloring agents and/or emulsifiers, e.g., lecithin. A cream is generally differentiated from a lotion, but this distinction usually depends on the degree of viscosity. According to this invention, a cream is also understood to include a lotion.

A "gel" in the sense of the present invention is the solution of a macromolecular substance, e.g., agarose, acrylic acid, alginic acid, polysiloxanes or acrylamide, the concentration of which is so high that the dissolved macromolecules are combined to form a spongy three-dimensional structure under suitable conditions and optionally with the addition of other substances (e.g., salts, acids, fillers, buffer substances) with a liquid in the cavities in the three-dimensional structure. Gels therefore have a relatively solid consistency. Their viscosity is between that of liquid and solid. Such a liquid is preferably pure $D_2O$ or a mixture of $D_2O$ and $H_2O$.

A "hydrogel" in the sense of the present invention is understood to refer to a gel which is characterized by an especially high capacity for uptake of water; in the sense of the present invention it preferably consists of 20-99% water, more preferably 70-99% and especially preferably 80-99% water without having the rheological properties of a traditional liquid. In an especially preferred embodiment, the hydrogel is transparent and at the same time spreadable without its morphology and integrity being impaired by spreading the gel.

Production of a formulation usable according to the present invention, in particular an ointment, cream or gel, is described in the examples. If such a formulation contains additional pharmaceutical and/or non-pharmaceutical active ingredients, they are preferably added by mixing the formulation. However, this may also be accomplished by any of the standard methods known in the prior art. Those skilled in the art will be familiar with such methods and also the concentrations to be selected of the components and/or substances to be used.

The concentrations of $D_2O$ in a formulation usable according to the present invention are preferably in the following ranges:

for a cream or ointment, preferably in the range from 0.1 wt % to 98 wt %, preferably from 5 wt % to 85 wt %, also preferably from 10 wt % to 80 wt %, especially preferably from 15 wt % to 70 wt %, more preferably from 20 wt % to 60 wt % and most preferably from 25 wt % to 50 wt % and for a gel, preferably 0.1 wt % to 99.8 wt %, preferably from 10 wt % to 99 wt %, also preferably from 15 wt % to 80 wt %, especially preferably from 20 wt % to 70 wt %, more preferably from 30 wt % to 70 wt % and most preferably from 35 wt % to 65 wt %.

Those skilled in the art will select the suitable concentration in particular on the basis of the prevailing indication, the condition of the body (patient) to be treated, the severity of the illness, etc.

In an especially preferred embodiment, a formulation usable according to the present invention contains at least one organic or inorganic solvent. The solvent is preferably selected from the group comprising ethanol, water and glycerol as well as mixtures thereof.

All the inventive uses and administrations of $D_2O$ disclosed in this description, e.g., with patches and bandages as well as layer systems may also be applied to the formulations usable according to the present invention without restriction unless otherwise indicated to the contrary.

The present invention is explained in greater detail below on the basis of examples which do not restrict the subject matters of the invention.

EXAMPLES

Example 1

Production of Hydrogels Based on Acrylic Acid 2.0 wt % carbopol 980 (manufacturer Noveon Inc., 9911 Brecksville Rd., Cleveland, Ohio 44141-3247, USA) was dissolved by stirring in pure $D_2O$, in pure $H_2O$ or in a mixture of $D_2O$ and $H_2O$ in separate batches and then titrated to a pH of 6.8 by pipetting 10M NaOH solution. Next the colorless, transparent and optically clear acrylic acid gels (carbopol gels) obtained by adding NaOH due to crosslinking of the polyacrylic acid via its carboxyl groups with the alkaline hydroxyl groups ($D_2O$ carbopol gel, $H_2O$ carbopol gel, $D_2O$/$H_2O$ carbopol gel) were stored at room temperature until further use, for at least 24 hours. $D_2O$ from the company Sigma-Aldrich (Munich) used in this and all following examples had an isotope purity of 99.0%.

Example 2

Production of Hydrogels Based on Siloxanes (Silicone)

In separate batches, 3.0 wt % hexamethyldisiloxane (brand name SILMOGEN CARRIER from DOW Corning) and 1 wt % ethanol were dissolved in pure $D_2O$, pure $H_2O$ or a mixture of $D_2O$ and $H_2O$ by stirring. These solutions were then mixed immediately with the gel (carbopol gel) prepared according to Example 1 in a weight ratio of 1:2 (silicone solution: carbopol gel) with vigorous stirring until obtaining optically transparent gels (silicone gels) ($D_2O$ silicone gel, $H_2O$ silicone gel, $D_2O$/$H_2O$ silicon gel). The gels were stored at room temperature for further use, for at least 24 hours.

Example 3

Production of Hydrogel Based on Alginates

In separate batches, 4.0 wt % alginic acid sodium salt (sodium alginate) (manufacturer Röhm GmbH, Darmstadt, Germany) was dispersed in pure $D_2O$, pure $H_2O$ or a mixture of $D_2O$ and $H_2O$ by stirring and then adjusted to a pH of 7.0 by titration by pipetting 10M NaOH solution. The resulting yellowish brown transparent gels (alginate gels) ($D_2O$ alginate gel, H₂O alginate gel, D₂O/H₂O alginate gel) were stored at room for further use, for at least 24 hours.

Example 4

Production of Hydrogel Based on PVA

In separate batches, 20 wt % polyvinyl alcohol (PVA C-25, Shin-Etsu Chemical Co., Japan) was dissolved in pure $D_2O$, pure $H_2O$ or a mixture of $D_2O$ and $H_2O$ by stirring. Then the solutions were subjected to five freeze-thaw cycles. The result was gels (PVA gels) ($D_2O$ PVA gel, $H_2O$ PVA gel, $D_2O/H_2O$ gel) with rubber-like properties which were cut into disks 2 mm thick. The gels were stored at room temperature for further use, for at least 24 hours.

Example 5

Production of Hydrogel Films and/or Plates Based on Agarose

In separate batches, 3.0 wt % agarose was dissolved in pure $D_2O$, pure $H_2O$ or a mixture of $D_2O$ and $H_2O$ and the solutions were then heated to 90° C. The $D_2O$ that was used from the company Sigma-Aldrich (Munich, Germany) had an isotope purity of 98.5%. The hot solutions were poured into suitable petri dishes to a height of 1.0-1.5 mm and cooled. The resulting gels (agarose gels) ($D_2O$ agarose gel, $H_2O$ agarose gel, $D_2O/H_2O$ agarose gel) were then stored under sterile conditions at 4° C.

Example 6

Production of Hydrogel Films and/or Plates Based on Acrylamide

Acrylamide gels (5% acrylamide) were produced and in separate batches pure $D_2O$, pure $H_2O$ or a mixture of $D_2O$ and $H_2O$ was degassed before adding the acrylamide (with 2.4% bisacrylamide) and heated to 40° C. After adding acrylamide and bis-acrylamide, the solutions were combined (Vortex mixer, 1 minute at 200 rpm) and then the catalysts tetramethylethylenediamine (TEMES, 1.0%) and ammonium persulfate (AP, 0.1%) were added, followed by mixing for 10 seconds. Then the gels were poured into petri dishes (height of the gel 1.0-1.5 mm) and stored for 2 hours at 40° C. The gels ($D_2O$ acrylamide gel, $H_2O$ acrylamide gel, $D_2O/H_2O$ acrylamide gel) were next washed, using a water mixture like that used for hydrating the gel (pure $D_2O$, pure $H_2O$ or a mixture of $D_2O$ and $H_2O$) for washing. The gels were stored at room temperature for further use, for at least 24 hours.

Example 7

Production of a Cream Containing $D_2O$

While stirring constantly at 40° C., $D_2O$ was added slowly to 50 g Asche cream base (manufacturer Asche Chiese GmbH, Hamburg, Germany) until reaching a weight amount of 38% $D_2O$ (based on the starting weight of the cream) in the homogenous mixture. The cream was the cooled to room temperature and sealed airtight and stored.

Example 8

Production of an Aerosol Containing $D_2O$

To create aerosols, only state-of-the-art equipment was used. A Pari LC Plus Universal atomizer (PARI GmbH, 82319 Starnberg, Germany) in combination with a Pari Universal compressor was used to produce a polydisperse aerosol at 200 mg/min with an average particle size (median mass diameter) of 2.5 μm for pure $H_2O$ and $D_2O$ and of 2.5-4.5 μm for $H_2O$ and/or $D_2O$ (operating pressure 2.0 bar, flow rate of the compressor air 6.0 L/min). The particle size measurement was performed by means of dynamic light scattering in a flow-through cuvette. The aerosol was produced at a temperature of 37° C. by corresponding thermostatic regulation of the atomizer in a thermostatically regulated water bath.

Example 9

Efficacy in a Cell Culture Test

After a closed monolayer had formed in the cell culture dish and after desmosomes had developed, human keratinocyte primary cultures produced according to H. M. Reinl et al. (J. Invest. Dermatol. 1995; 105(2):291-5) were incubated with cell culture medium additionally containing 35 wt % $D_2O$ (sample) and/or $H_2O$ (controls). On the day of incubation, the sample and controls were infected with HSV-1. The infection was accomplished by adding the virus to the cell culture medium ($10^7$ viruses per cell culture dish in 1 mL cell culture medium). After 3 days (after infection), the sample and control groups were tested for the average number of viral particles per cell. The virus count was performed using a transmission electron microscope according to standard fixation and staining methods (glutaraldehyde and osmium tetroxide). In each case, 20 randomly selected keratinocyte cells from the sample group and the control group were evaluated with regard to the viral particles contained in them.

The resulting average virus count was 10±4 for the sample group ($D_2O$) and 28±4 for the control group ($H_2O$).

Example 10

Efficacy in an Animal Experiment

The backs of 12 guinea pigs were infected with HSV-1 by means of a vaccination instrument as described in detail by M. B. McKeogh et al. (Arch. Dermatol. 2001, 137, 1153-1158). Immediately after infection, the guinea pigs were divided into four randomized groups of three animals each. In sample group, every 3 hours, a carbopol acid gel prepared according to Example 1 with 100% $D_2O$ was applied to the backs of the animals (to an area of approximately 12 cm²) (approximately 1.0 gram of gel per application). Sample group 2 received exclusively drinking water to which 35% $D_2O$ had been added and received no other treatment. Control group 1 received a similar amount of carbopol acid gel at identical points in time applied to the backs of the animals; the gel had been prepared according to Example 1 from 100% $H_2O$ ($H_2O$ carbopol gel). Control group 2 was not subjected to any further treatment after infection. After five days, the animals were sacrificed and the severity of the infection was analyzed by determining the number and size of lesions (papules and ulcerations). Furthermore, the average number of HSV-1 particles per keratinocyte cell (back) was measured by electron microscopy as described in Example 9.

The result is shown in Table 1, illustrating the superior effect of $D_2O$ applied topically (sample group 1) in comparison with $H_2O$ or no treatment (control groups 1 and 2) with respect to inhibiting the number of lesions and their area as well as the number of HSV-1 cells per cell. A virustatic effect of $D_2O$ could also be detected in drinking water (sample group 2) but the effect here was not as pronounced as the effect of topical D$_2$O application (sample group 1).

Example 11

Efficacy for Treatment of HSV-1 in a Clinical Trial, Comparison with Aciclovir For this study, 32 healthy volunteers between the ages of 23 and 58 (16 female, 16 male) were selected. All the test subjects selected had a history of herpes labialis which is triggered in particular by sunlight (UV radiation). None of the test subjects used any antiviral therapeutic agents or immunomodulating therapeutic agents for 1 week prior to or during the test which was limited to 10 days.

For all test subjects, first the individual minimum erythematous dose (MED) was determined by exposing six areas, each measuring 1 cm$^2$ on the upper arm of the respective test subject, to UV light for one to six minutes (time increment between irradiation of the six areas: one minute each, the unexposed areas being covered). The UV light source was two model FS 20 fluorescent lamps from Westinghouse, Bloomfield, N.J., USA, with the emitted radiation power being measured on each test subject prior to application using a radiation meter (Radiant Power meter, model 70260 with a measurement head, model 70268 from Newport, Irvine, Calif., USA). During irradiation, the UV light source was a distance of 20 cm away from the skin area to be exposed to UV light. The UV-exposed areas of the test subject were evaluated after 24 hours and the MED was determined as the shortest period of time after which an area exposed to UV light would have a distinct edge of the erythema after 24 hours.

After determining the individual MEDs, the lip area of each test subject was divided into four regions (right and left upper lip and right and left lower lip). UV light exposure was performed only in areas which had been identified by the test subject previously as the most common sites of herpes labialis recurrences. The portion of the lips not to be exposed to UV light was protected with a sunscreen (sun protection factor 50) before exposure. The lip area to be UV-exposed received a radiation dose of 4×MED, which was intended for the respective test subject. The skin around the lips to be UV-exposed was protected by a mask and/or by a sunscreen (sun protection factor 50), resulting in a strip of skin 0.8-1.0 cm away from the edge of the lip also being exposed to UV. Then the 32 test subjects were randomly assigned to four groups of eight people each.

The four test groups were treated differently. Immediately after the radiation exposure and from this point in time every 2.5 hours (except at night) the UV-exposed lip area on eight test subjects each was treated by application of D$_2$O carbopol gel (prepared according to Example 1 with 100% D$_2$O), H$_2$O carbopol gel (placebo, prepared according to Example 1 with 100% H$_2$O), Zovirax cream (aciclovir in a cream dispenser from GlaxoSmithKline) or a D$_2$O cream prepared according to Example 7 into which 20 wt % Zovirax cream had additionally been incorporated homogeneously.

The test subjects were tested on days 2, 3, 5, 7, 9 and 15 after radiation exposure. The number of new lesions (vesicles and ulcerations) as well as their maximum extent were determined. The area of calculation of the maximum extent was performed under the assumption of a circular shape whose average diameter was determined from three measurements on each lesion. Test subjects having new lesions were inspected daily for additional new lesions on each of the four following days after they were found and the size of all lesions was measured. The lesions were subdivided in the following classes:
- direct lesions formed within 48 hours after the radiation exposure
- indirect lesions formed after this period of 48 hours had elapsed and
- reduced lesions that were defined as such and occurred at any point in time but did not develop beyond a just barely perceptible elevation of the skin affected (papules).

Figure 2:
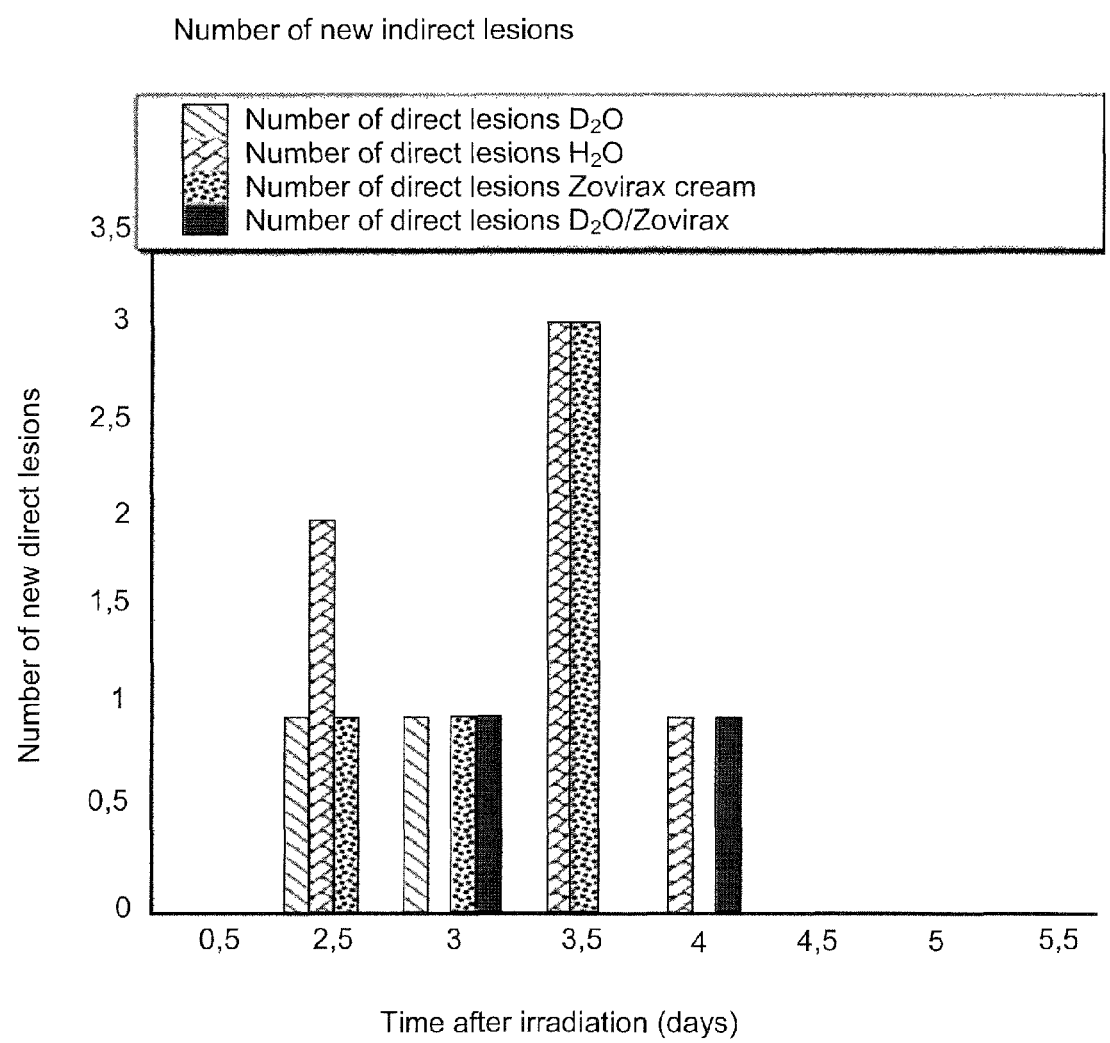
FIG. 2 shows a diagram of new indirect lesions occurring. The number of new indirect lesions in the period of time up to fifteen days after UV irradiation for four test groups of eight test subjects each, who were treated as follows beginning after irradiation (Example 11): every 2.5 hours (except at night) the UV-exposed lip area of eight test subjects was treated with D₂O gel (prepared according to Example 1 with 100% D₂O), with H₂O gel (placebo, prepared according to Example 1 with 100% D₂O), with Zovirax cream (aciclovir in a cream dispenser from GlaxoSmithKline) or with a D₂O cream prepared according to Example 7 into which an additional 20 wt % Zovirax cream had been incorporated homogeneously.
Figure 3:
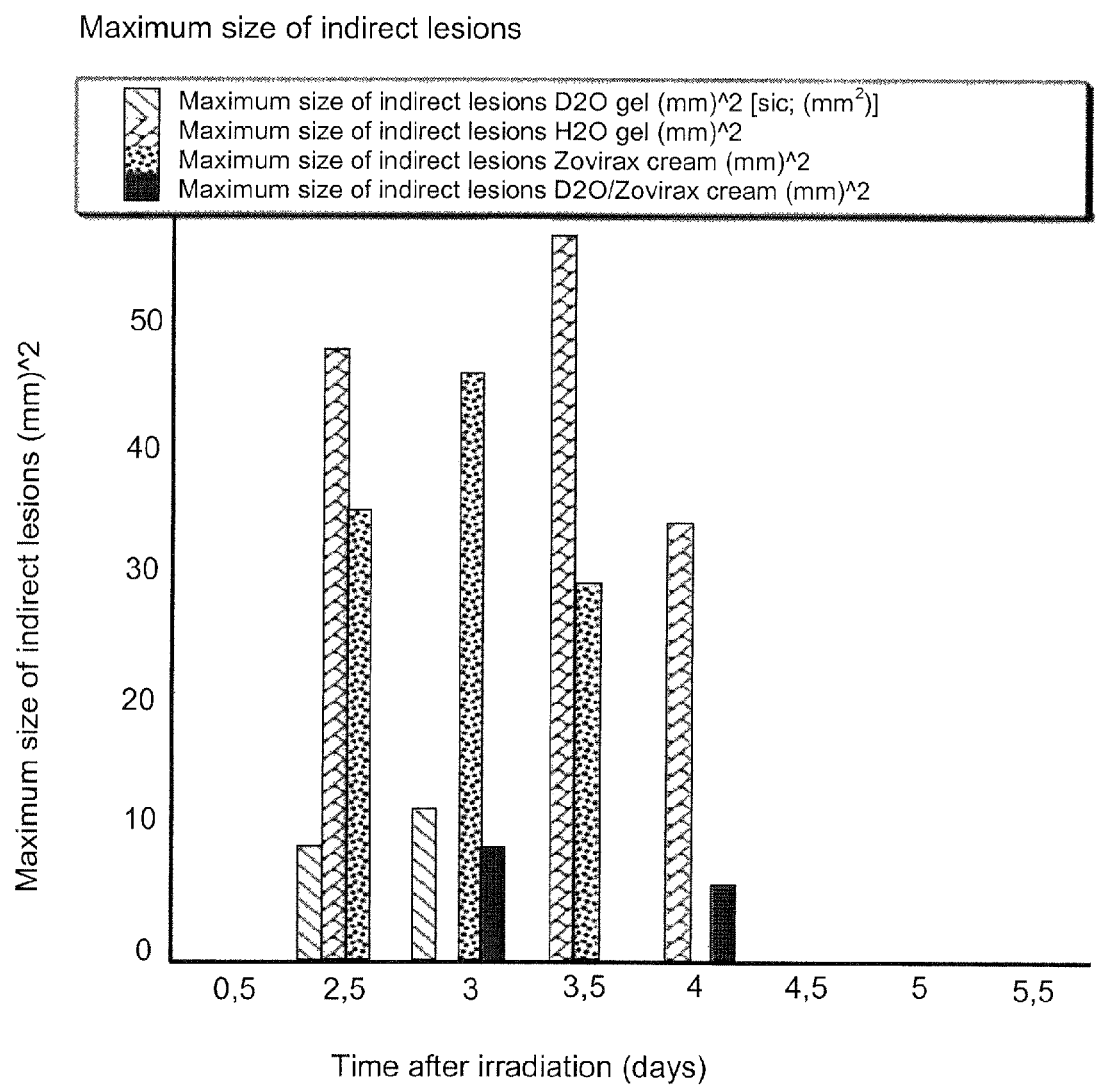
FIG. 3 shows a diagram of the maximum size of indirect lesions occurring. The maximum size of the indirect lesions shown in FIG. 2 for the four test groups is shown. The values shown here for the area covered by the lesions represent the averages of the maximum areas of the individual indirect lesions determined for the respective test group.

FIG. 1 shows the number of direct lesions in the period of time of up to two days after the radiation exposure for the four test groups. FIG. 2 shows the number of indirect lesions in the period of time from two to fifteen days after the radiation exposure for the four test groups. FIG. 3 shows the maximum size of the indirect lesions for the four test groups as a function of the day on which the maximum was found. Table 2 lists the total number of observed direct and indirect lesions for the four test groups.

In summary, these results show a definite and long-lasting effect of D$_2$O to suppress lesions in comparison with the placebo (H$_2$O). In addition, this effect of D$_2$O is definitely superior to that of a commercial aciclovir cream (Zovirax) in terms of the number of lesions as well as the maximum extent thereof. A D$_2$O cream containing 20% Zovirax also has an effect which is definitely superior in both areas (number of lesions and extent of lesions) to the pure commercial Zovirax cream. In none of the four test groups were adverse effects of the treatment with the pharmaceutical preparations that were used observed.

Example 12

Efficacy of D$_2$O for HSV-2 Treatment in a Clinical Trial

Ten healthy volunteers between the ages of 21 and 60 (six females, four males) were selected for this study. All selected test subjects had a history of recurring genital herpes (HSV-2) confirmed by PCR tests. None of the test subjects used any antiviral therapeutic agents or immunomodulating therapeutic agents for four weeks before or during the test, which was limited to six months. According to reports by the individual test subjects, the average number of HSV-2 relapses per year was 4.2±2.5 (standard deviation for all ten test subjects). The test subjects were randomly assigned to two groups (one sample group, one control group) of five people each and were divided according to a single blind scheme.

The sample group received a D$_2$O silicone gel with 100% D$_2$O prepared according to Example 2; the control group received H$_2$O silicone gel with 100% H$_2$O prepared according to Example 2. Both groups were instructed to apply the respective gel every 3 hours (except at night) for a period of five days to the affected sites at the slightest sign of a recurrence, i.e., initial development of lesions (papules and/or ulcerations), and starting at this point in time of the initial application, to measure the duration of the lesion (recurrence lesion) in days. Only results in which there was at least a perceptible development of a lesion were counted. After six months, the test was ended and the reports of the test subjects were analyzed.

Results:
a) Control group (H$_2$O silicone gel): average number of recurrences in six months per test subject: 2.4±1.5; average duration: 5.5±1 days b) Sample group (D$_2$O silicone gel): average number of recurrences in six months per test subject: 2.2±1.5; average duration: 2.0±1 days These results show a clear efficacy of the D$_2$O silicone gel to reduce the duration of an HSV-2 recurrence. No adverse effects were observed by the test subjects.

Example 13

Efficacy of D$_2$O for Treatment of Warts of HPV-Based Warts in a Clinical Trial Ten health volunteers between the ages of 21 and 41 (five females, five males) were selected for this study. All the selected test subjects had a history of warts of the verrucae vulgares type which were manifested in particular on the fingers. Only test subjects who had warts of this type on at least two fingers were selected.

In all test subjects, first the stratum corneum of the warts was removed on two fingers by local cryogenic treatment using liquid nitrogen. On the next day, the treated warts were measured with regard to their volume protruding above the skin by a noncontact optical method (3D wart measurement by strip projection system ATOS-1 from the company GOM, Bibertal Ulm, Germany) and the data for each test subject and for each individual wart was recorded.

Then the test subjects were randomly assigned to two groups (sample group and control group) of five people each. In the sample group, 1.5 mm thick D$_2$O agarose gel squares produced according to Example 5 (gel cut into squares 1 cm$^2$ in size, prepared from pure D$_2$O) were applied directly to the warts and secured in a semiocclusive dressing using a Tegaderm patch applied above the gel (type 16004 from 3M Corp., Minneapolis, USA) cut to a size of 5 cm×2 cm. In the control group under otherwise identical conditions, an H$_2$O agarose gel prepared by a similar method according to Example 5 was applied to the warts and secured there. In both groups, at least three warts were treated in this way per test subject.

After five days, patches and gels were removed and the wart volumes were measured optically. From the comparison with the individual wart volumes determined before application of the gels, the percentage increase in volume was calculated. By forming the average, the average percentage increase in volume <% V$_w$> of the warts of the respective group was calculated.

Results:
Control group <% V$_w$>=(190±20) %
Sample group <% V$_w$>=(105±5) %

For the sample group (D$_2$O agarose gel) the wart volume had not increased in the observation period within the range of measurement error.

Efficacy of D$_2$O in HSV-1 infected guinea pigs (Example 10). This shows the average number and size of lesions as well as the average number of HSV-1 cells per keratinocyte cell (each based on the area of the back treated with the gel) five days after infection with HSV-1. Immediately after infection, the four groups of three animals each were treated as follows: sample group 1 received a D$_2$O carbopol gel prepared according to Example 1 with 100% D$_2$O applied to the back of the animal every 3 hours (approximately 1.0 gram of gel per application). Control group received an equal amount of an H$_2$O carbopol gel (from 100% H$_2$O) prepared according to Example 1 and applied at identical points in time. Sample group 2 received only drinking water to which 35% D$_2$O had been added and did not receive topical application of a gel. Control group 2 was not subjected to any further treatment after infection.

TABLE 1

|  | Average number of lesions | Average size of lesions (mm$^2$) | Average number of HSV-1 viral particles per cell |
|---|---|---|---|
| Sample group 1 (D$_2$O carbopol gel) | 2 | 16 ± 3 | 6 ± 3 |
| Sample group 2 (D$_2$O in drinking water) | 3 | 19 ± 3 | 11 ± 4 |
| Control group 1 (H$_2$O carbopol gel) | 9 | 25 ± 3 | 24 ± 4 |
| Control group 2 | 10 | 23 ± 3 | 26 ± 4 |

The total number of direct and indirect lesions on a total of 32 test subjects in a period of time up to fifteen days after UV radiation exposure (Example 11). According to the above data (Example 11), direct lesions occur in the period of time up to two days after radiation exposure, indirect lesions occur in the period of time from two to fifteen days. Immediately after radiation exposure and from this time on, the UV-exposed lip area on each of the eight test subjects of the four test groups was treated every 2.5 hours (except at night) with D$_2$O carbopol gel (prepared according to Example 1 with 100% D$_2$O), with H$_2$O carbopol gel (placebo, prepared according to Example 1 with 100% H$_2$O), with Zovirax cream (aciclovir in a cream dispenser from GlaxoSmithKline) or with a D$_2$O cream prepared according to Example 7 to which 20% Zovirax cream had also been added homogeneously.

TABLE 2

| Gel/cream | Indirect lesions (total number) | Direct lesions (total number) |
|---|---|---|
| D$_2$O carbopol gel | 2 | 1 |
| H$_2$O carbopol gel | 6 | 8 |
| Zovirax cream | 5 | 5 |
| D$_2$O/Zovirax cream | 2 | 1 |

I claim:

1. A method for treating a herpes virus-based disease of the skin wherein said method comprises topically administering deuterium oxide to the skin of a subject suffering from a herpes virus-based disease of the skin, whereby the deuterium oxide is administered at a site of herpes viral replication in an amount effective to limit herpes viral replication in the skin by raising the level of deuterium oxide, thereby treating the herpes virus-based disease of the skin.

2. The method, according to claim 1, wherein the herpes virus-based disease of the skin is caused by herpes simplex virus type 1, herpes simplex virus type 2 or varicella zoster virus.

3. The method, according to claim 1, wherein the herpes virus-based disease of the skin is selected from the group consisting of herpes labiales, herpes nasalis, keratoconjunctivitis herpetica, stomatitis herpetica, herpes facialis, herpes buccalis, herpes genitales, herpes perianalis, herpes glutealis and herpes zoster.

4. The method, according to claim 1, wherein the deuterium oxide is used in combination with at least one additional pharmaceutical agent and/or at least one additional non-pharmaceutical agent.

5. The method, according to claim 4, wherein the at least one additional pharmaceutical agent is selected from the group consisting of virustatics, proteins, peptides, nucleic acids and immunosuppressant ingredients.

6. The method, according to claim 4, wherein the at least one additional non-pharmaceutical agent is selected from the group consisting of pharmaceutically tolerable organic or inorganic acids or bases, polymers, copolymers, block copolymers, monosaccharides, polysaccharides, ionic and nonionic surfactants or lipids and mixtures thereof, albumin, transferrin and DNA repair proteins.

7. The method, according to claim 1, wherein the deuterium oxide is topically administered with a patch or a bandage.

8. The method, according to claim 7, wherein the patch or bandage is used in combination with at least one membrane or at least one film.

9. The method, according to claim 8, wherein the membrane is a microporous or nanoporous membrane.

10. The method, according to claim 8, wherein the film is a microporous or nanoporous film.

11. The method, according claim 1, wherein the deuterium oxide is topically administered as an aerosol.

12. The method, according to claim 1, wherein the deuterium oxide is administered in a formulation selected from the group consisting of an ointment, a cream, a gel and a hydrogel.

13. The method of claim 1, wherein the subject is a human.

14. The method, according to claim 13, wherein the herpes virus-based disease of the skin is herpes labiales.

15. The method, according to claim 13, wherein the herpes virus-based disease of the skin is selected from the group consisting of herpes labiales and herpes nasalis.

16. The method, according to claim 13, wherein the herpes virus-based disease of the skin is selected from the group consisting of herpes labiales and herpes facialis.

17. The method, according to claim 13, wherein the herpes virus-based disease of the skin is selected from the group consisting of herpes labiales and herpes genitales.

18. The method, according to claim 13, wherein the herpes virus-based disease of the skin is selected from the group consisting of herpes labiales and herpes perianalis.

19. The method, according to claim 13, wherein the herpes virus-based disease of the skin is selected from the group consisting of herpes labiales and herpes glutealis.

20. The method, according to claim 13, wherein the herpes virus-based disease of the skin is selected from the group consisting of herpes labiales and keratoconjunctivitis herpetica.

* * * * *